United States Patent

Dohlsten et al.

[11] Patent Number: 5,858,363
[45] Date of Patent: Jan. 12, 1999

[54] TARGET SPECIFIC ANTIBODY-SUPERANTIGEN CONJUGATES AND THEIR PREPARATION

[75] Inventors: Mikael Dohlsten, Lund; Eva Akerblom, Uppsala; Gunnar Hedlund, Lund; Peter A. Lando, Malmo, all of Sweden

[73] Assignee: Pharmacia & Upjohn AB, Italy

[21] Appl. No.: 485,706

[22] Filed: Jun. 7, 1995

Related U.S. Application Data

[63] Continuation of Ser. No. 339,279, Nov. 8, 1994, abandoned, which is a continuation of Ser. No. 961,937, Jan. 14, 1993, abandoned.

Foreign Application Priority Data

Jul. 20, 1990 [SE] Sweden ................................ 9002479
Jul. 20, 1990 [SE] Sweden ................................ 9002484

[51] Int. Cl.$^6$ ...................... A61K 39/395; A61K 39/385; C07K 16/00
[52] U.S. Cl. ...................... 424/183.1; 424/178.1; 424/179.1; 424/193.1; 424/277.1; 424/165.1; 424/237.1; 530/391.1; 530/391.7; 530/391.9
[58] Field of Search ...................... 530/391.1, 391.9; 424/178.1, 179.1, 183.1, 193.127, 277.1, 165.1, 237.1

[56] References Cited

U.S. PATENT DOCUMENTS 4,545,985  10/1985  Pastan .................................. 424/85.91

FOREIGN PATENT DOCUMENTS

| | | |
|---|---|---|
| A2 0240200 | 10/1987 | European Pat. Off. . |
| A2 0336943 | 3/1989 | European Pat. Off. . |
| A2 3036943 | 3/1989 | European Pat. Off. . |
| 0334300 | 9/1989 | European Pat. Off. . |
| 334300 | 9/1989 | European Pat. Off. . |
| A2 0332174 | 9/1989 | European Pat. Off. . |
| A2 0336405 | 10/1989 | European Pat. Off. . |
| A-376 746 | 12/1989 | European Pat. Off. . |
| 510949 | 1/1997 | European Pat. Off. . |
| 2 197 323 | 5/1988 | United Kingdom . |
| WO-A-85/03508 | 8/1985 | WIPO . |
| A1 8800703 | 1/1988 | WIPO . |
| A1 8905816 | 6/1989 | WIPO . |
| WO-A-90/11779 | 3/1990 | WIPO . |
| WO-A-91/04053 | 4/1991 | WIPO . |

OTHER PUBLICATIONS

Dohlsten et al., Proc. Natl. Acad. Sci. USA., vol. 88, pp. 9287–9291, Oct. 1991.
Alber et al., J. Immunol. 144 (190) 4501–4506.
Carlsson et al., Biochem. J. 173 (1978)723–737.
Dohlsten et al., Immunol. 71 (1990) 96–100.
Endo et al., Cancer Res. 48 (1988) 3330–3335.
Fleischer et al., J. Exp. Med. 167 (1988) 1697–1707.
Ghose et al., J. Natl. Cancer Inst. 61 (1979) 657–676.
Hedlund et al., Cell. Immunol 129 (1990) 426–34.
Houghton and Southby, Synth. Commun. 19 (18) (1989) 3199–3209.
Hufnagle et al., Infect. Immun. 59 (1991) 2126–2134.
Ishizaka et al., Cell. Immunol. 118 (1989) 100–107.
Jullien et al., Tetrahedron Letters 29 (1988) 3808–06.
Larsson et al., Int. J. Canc. 42 (1988) 877–82.
Nakatsuji, Kawamura and Okahara, Synthesis (1981), p. 42.
Ochi and Wake, ULCA–Symposium: Cellular Immunmity and the Imuumontherapy of Cancers, Jan. 27–Feb. 3, 1990, Abstract CE 515, p. 109.
Opitz et al., Immunobiol. 160 (1982) 483–453.
Platsoucas et al., (Cell Immunol. 97 (1986) 371–385.
Slama and Rando, Carbohydrate Research 88 (1981) 213–221.
Slama and Rando, Biochemistry 19 (1980) 4595–4600.
White et al., Cell 56 (1989) 27–35.
Biotechnology vol. 7, Jun. 1989 R. Carlson, "Monoclonal Antibodies into the 90 'S".
Legaard et al. Cellular Immunology 135, Jul. 1991 pp. 372–382 The Superantigen *Pseudomonas* Exotoxin A Requies Additional Functional from accessory cells for T lymphocyte proliferation.

Science vol. 11 May 1990, Philippa Marrack & Johon Kappler, The Staphylococcal Enteroxtoxins and Their relatives —pp. 705–708.
Batra et al (1989) Proc. Natl. Acad. Sci. USA 86:8545–9.
Batra et al (1991) Mol. Cellular Biol. 1/(4):2200–2205.
Kalland et al (1993) Med. Oncol. & Tumor. Pharmacothe, 10(½)= 37–47.
"Monoclonal Antibody —Superantigen Fusion Proteins: Tumor Specific Agents for T Cell Based Tumor Therapy"; Dohlsten et al., Proc. Nalt. Acad. Sci. USA., vol. 91, pp. 8945–8949, 1994.
Osband et al (1990) Immunology Today 11(6)= 193–195.

*Primary Examiner*—Ponnathapura Achutamurthy
*Assistant Examiner*—P. Ponnaluri
*Attorney, Agent, or Firm*—Fulbright & Jaworski L.L.P.

[57] ABSTRACT

A soluble antibody conjugate comprising an antibody linked to a structure which is recognizable by T-cells and has the ability to direct T-cells to lyse the target cell, which is recognized by the antibody. The conjugate is characterized by the structure being a superantigen. One important mode is a method for the lysis of target cells, wherein the target cells are contacted with a target cell lysis effective amount of the conjugate. The method of lysis is part of a potent treatment regime for cancer, autoimmunity, parasitic infestations and fungal, viral and bacterial infections The specification also describes modes such as the synthesis of the conjugate and pharmaceutical compositions and their manufacture.

73 Claims, 3 Drawing Sheets

TARGET SPECIFIC ANTIBODY-SUPERANTIGEN CONJUGATES AND THEIR PREPARATION

This application claims priority as a continuation of U.S. application Ser. No. 08/339,279, filed Nov. 8, 1994, abandoned, which is a continuation of U.S. application Ser. No. 07/961,937, filed Jan. 14, 1993, abandoned, which is based upon PCT application number PCT/SE91/00496, international filing date Jul. 16, 1991, which is based upon Swedish patent application numbers 9002484-5 and 9002479-5, both filed Jul. 20, 1990.

The present invention concerns antibody conjugates which are capable of activating cytotoxic T-cells (CTLs). The conjugates are useful for destroying undesired cells that are associated with i.a. cancer forms, autoimmune processes, parasitic infestations and bacterial, viral and fungal infections.

BACKGROUND OF THE INVENTION.

Attempts have been made over the past years to use antibodies in combination with agents that directly exert a toxic effect on target cells (cytotoxic agents, cytotoxins) in order to provide a selective action on target cells and to prevent and minimize the non-specific effect on other cells. The combinations suggested have ranged from covalently bonded complexes using linkage-providing molecules and non-covalently bonded complexes to simple mixings (e.g. Ghose et al., J. Natl. Cancer Inst. 61(1979)657–676 and Carlsson et al., Biotechnology 7(1989)567–73). Suggested cytotoxins-have been i.a. diphteria toxin, ricin, subunit A of ricin, gelonin, and Pseudomonas aeruginosa exotoxin A (Takeda Chemical Ind., EP-A-336,405 and Pastan et al., WO-A-88/00703, both of which have been cited in connection with the priority application, SE-9002479).

With the advent of the hybridoma technology and the accompanying availability of monoclonal antibodies, it has been feasible to use the concept of complexes between antibodies and cytotoxic agents to more specifically direct the cytotoxic agents to the intended target cell population.

In view of the recognized damaging effect of cytotoxic agents on other cells than target cells, one has suggested to replace the cytotoxic agents with immune stimulators that trigger T-lymphocytes and activate CTLs. Specific proposals have been concerned with antibodies conjugated to (i) antibodies that are directed against a T-cell receptor or compounds that are able to bind to a T-cell receptor (Mass. Inst. Techn., EP-A1-180,171);

(ii) compounds, such as antigens, mitogens, other foreign proteins, and peptides that activate cytotoxic T-cells (Neorex Corp., EP-A1-334,300);

(iii) MHC antigens, (Behringwerke AG, EP-A1-352,761);

(iv) antigens against which the individual to be treated has immunity, (Med. Res. Counc. WO-A-90/11779 (publ. 1990-10–18)); and (v) an unnamed bacterial enterotoxin (Ochi and Wake, UCLA-Symposium: Cellular Immunity and the Immunotherapy of Cancers, Jan. 27–Feb. 3, 1990, Abstract CE 515. page 109).

However, the immune stimulators suggested hitherto have been either too specific or too general in their action. For instance classical antigens activate only about 1 out of $10^5$ T-cells while mitogens are potentially capable of activating a majority of the T-cells.

It has been recognized that certain-agents mediate activation of a moderate ratio of T-cells; i.e. they activate T-cells at a relatively high frequency, but far from 100% (Fleischer et al., J. Exp. Med. 167(1988)1697–1707; and White et al., Cell 56(1989)27–35, both articles being incorporated by reference). This type of agents are more effective activators than classical antigens and they accordingly have been named superantigens (for a review see Kappler and Marrack, Science 248:705,(1990)). It has further been demonstrated (Dohlsten et al., Immunol. 71(1990)96–100; and Hedlund et al., Cell. Immunol 129(1990)426–34, both articles being incorporated by reference) that the superantigens known so far have the capacity to bind to MHC Class II molecules on target cells and activate cytotoxic T-cells bearing the proper T-cell receptor V beta chain. The published data indicate that the MHC binding is a prerequisite for T-cell binding and activation to occur. It can not be excluded that in the future superantigens will be found that act through a T-cell receptor V alpha chain or other surface structures only found on subpopulations of T-cells.

The immunomodulatory effect of the superantigen Staphylococcus enterotoxin A (SEA) has also been described by Platsoucas et al (Cell Immunol. 97(1986)371–85).

Most of the presently known superantigens have earlier been recognized as toxins and all of them have been of microbial origin. Staphylococcal enterotoxins for instance are enterotoxic and activate T-cells, and the two effects are discernible from each other (Fleischer et al., Cell. Immunol. 118(1989)92–101; Alber et al., J. Immunol 144(1990) 4501–06; and Infect. Immun. 59(1991)2126–34).

It has previously been suggested to use superantigens in order to direct CTL mediated lysis of cells carrying MHC Class II antigens (Pharmacia AB, WO-A-91/04053, publ. 1991-04–04). WO-A-91/04053 covers, but does not explicitly mention, superantigens that are incorporated into covalent immunoconjugates.

Cells lacking MHC Class II or expressing marginal amounts of MHC Class II proteins do, however, not bind sufficient amounts of superantigens in order to efficiently direct lysis of them by CTLS. Thus due to the general abundance of cells carrying MHC Class II antigens and the non-abundance of MHC Class II antigens on most tumour cells, superantigens should be of low value for the specific killing of such unwanted cells.

However, we have found that a specific cell-killing effect mediated by CTLs can be achieved with superantigens, if they are covalently linked to an antibody directed against an epitope that is specific for the cell to be killed. The activation of the immune system may induce target cells lacking MHC Class II antigens to express them, which may potentiate the desired lytic effect.

SUMMARY OF THE INVENTION

The present invention provides novel antibody conjugates (i) comprising (1) an antibody directed against target cells, and (2) a superantigen, i.e. a structure that is recognized (interact with or bind to) and activate T-cells, in particular CTLs;

(ii) methods for destroying target cells, in particular in connection with therapeutical treatment methods contemplated on mammals, and for specific activation of T-cells, such as CTLs;

(iii) method of synthesis for the conjugates; and (iv) pharmaceutical compositions containing the conjugates and preparation methods for the compositions.

The methods for destroying target cells encompasses therapeutic treatment methods for cancer, autoimmunity, viral infections, bacterial infections, fungal infections, parasitic infestations and other diseases in which the objective is to kill certain cells with a high degree of accuracy. The conjugates of the invention may be used for the manufacture of pharmaceutical compositions intended to be used for destroying target cells associated with the diseases just given. The individuals to be treated are normally animals, primarily human beings.

DETAILED DESCRIPTION OF THE INVENTION

Superantigen part of the conjugate

The novel antibody conjugates are characterized by the structure that is recognized by the T-cells being a superantigen. The conjugates are normally so (iii) straight, branched or cyclic hydrocarbon chains which are saturated and which possibly may be substituted with one or more hydroxy or amino groups;

(iv) ether (—O—, where each of the free valencies binds directly to a saturated carbon-atom); and (v) primary amine or disubstituted hydrazine (—NH— or —NH—NH—, respectively, where each of the free valencies binds directly to a saturated carbon atom).

The length of the bridge should be within the ranges normally contemplated within the technical field, i.e. shorter than 180 atoms, such as <100 atoms, but longer than 3–6, preferably longer than 16 atoms.

The preferred linkage is hydrophilic and should not contain any aromatic ring. Preferred hydrophilic structures that may form part of the linkage —B— are: (i) polypeptide chains of the naturally occurring hydrophilic alpha amino acids (e.g. asparaginic acid and its amide, glutaminic acid and its amide, lysine, arginine, glycine, threonine, serine and possibly also histidine); (ii) oxaalkylene chains such as (—O($CH_2$)$_n$)$_{n'}$- where n is an integer 2–5, preferably 2–3, and n' may be an integer 1–20; and (iii) —S— (thioethers), —O— (ethers) and unsubstituted amides (—CONH—) all of which being linked to short unsubstituted hydrocarbon chains ($C_{1-4}$), preferably containing 1 or 2 carbon atoms.

Hydrophilic amino acids may be present in hydrophilic structures of the type (F—(Pro)$_n$)$_m$F, wherein F represents an amino acid sequence, preferably 4–8 residues, in which each amino acid is individually selected from serine, glycine and threonine, m is an integer 1–4 and n an integer 4–8 (Cetus Corp., WO-A-85/03508).

The linkage —B— may be attached either at specific locations in the antibody or superantigen part of the conjugate or at random. Potential locations are an amino terminal, a carboxy terminal and a lysine residue (omega amino group). If the antibody or superantigen carries a thiol group or disulfide group (cystine or cysteine, respectively) these groups may also be used for covalently coupling, unless they are not essential for the activity of the active parts of the conjugate. When present, carbohydrate structures can be oxidized to aldehyde groups that in turn may used for linking to the other moiety of the conjugate (cf. Cetus Corp., EP-A-240,200).

The conjugate of the invention should not contain any significant amounts of ester bonds and labile amide bonds, in particular not formed with tyrosine and histidine residues, respectively. If such bonds have been formed during the synthesis they can be removed by use of hydroxylamine (Endo et al., Cancer Res. 48(1988)3330–3335).

The number of superantigen moieties that may be present per antibody active moiety is normally 1–5, preferably 1 or 2.

In one of the preferred modes the conjugate substance shall be substantially uniform with regard to superantigen per antibody, and/or employed binding positions in the superantigen and antibody moieties, respectively, and/or linkage —B— etc. In other words all the individual conjugate molecules in conjugate substance should be the same in regard to these variables.

The substance should be essentially free from unconjugated antibodies or unconjugated superantigens.

The exact ratio superantigen to antibody, linkage structure etc. for the optimal conjugate will depend on the selected monoclonal (including class, subclass, producing clone, specificity) and selected superantigen. The experimental models given in this specification will enable the screening for optimal parameters also for other superantigens and other antibodies.

According to the embodiment of the invention studied most extensively up to the filing date, the linkage —B— comprises the structure $$—S_rRCONHCH_2CH_2(OCH_2CH_2)_nO(CH_2)_mCOY— \quad (I)$$

The free valencies in formula I link to the active parts, respectively. This takes place either directly or through further divalent inert structures that are comprised within the bridge —B—.

n is an integer >0, e.g. 1–20, preferably 2 or >2 and in many cases <10. m is 1 or 2.

S is a sulphur atom and binds directly to a saturated carbon atom at each of its valencies (—$S_r$—=a thioether or a disulfide). r is an integer 1 or 2.

Y is —NH—, —NHNH— or —NHN=CH— that at their left ends bind to the CO group shown in the right terminal in formula I and at their right ends to a saturated carbon atom or to a carbonyl group (only when Y equals —NHNH—).

R is preferably alkylene (having 1–4 carbon atoms, often 1 or 2 carbon atoms), that possibly is substituted with one or more (1–3, in the preferred case <2) hydroxy (OH) groups.

Preparation of the antibody-superantigen conjugate

The antibody conjugates of the present invention can be obtained by enriching and purifying them from culture media of cells producing them, or from other media in which they have been synthesized.

The synthesis of our novel conjugates may be accomplished by techniques known in the art for conjugate synthesis, i.e. genetic engineering (recombinant techniques) or via the appropriate antibody and superantigen by classical coupling reactions at appropriate functional groups. The functional groups present in proteins and normally utilized are:

(i) Carbohydrate structures. This structure may be oxidized to aldehyde groups that in turn are reacted with a compound containing the group $H_2$NNH— to the formation of a —C=NH—NH— group.

(ii) Thiol group (HS—). The thiol group may be reacted with a compound containing a thiol-reactive group to the formation of a thioether group or disulfide group. Free thiol groups of proteins are present in cystine residues and may be introduced onto proteins by thiolation or splitting of disulfides in native cysteine residues.

(iii) Free amino groups ($H_2$N—) in amino acid residues. An amino groups may be reacted with a compound containing an electrophilic group, such as an activated carboxy group, to the formation of an amide group. The free amino group preferably is an amino terminal or the omega amino group of a lysine residue.

(iv) Free carboxy groups in amino acid residues. A carboxy group may be transformed to a reactive (activated) carboxy group and then reacted with a compound containing an amino group to the formation of an amide group. However, precautions must then be taken to minimize amide formation with the amino groups that mostly are present together with carboxy groups in the same protein. The free carboxy group preferably is a carboxy terminal or a carboxy group of a diacidic alpha amino acid.

The compounds carrying a $H_2$NNH— group, a thiol-reactive group, an activated carboxy group, or an amino group may be bifunctional coupling reagents or an antibody or a superantigen. The groups are bound directly to saturated carbon atoms except for the $H_2NNH$— group that as an alternative also may be bound to a carbonyl carbon. The groups may have been introduced onto the the antibody or superantigen by common derivatization.

Recombinant techniques provide efficient means for the manufacture of conjugates in which the parts are specifically linked together from a terminal carboxy group in one moiety to a terminal amino group in the other moiety. A linkage structure consistent with the technique applied may be inserted. The reagents employed are selected so that they will provide the linkage —B— as defined above. Common bifunctional reagents have the formula Z—B'—Z— where Z and Z' are are functional groups that are mutually consistent with each other and allowing for covalent coupling at a functional group present on a protein. See above. B' is an inert bridge that may contain the same structures as given for the linkage —B— above. Particularly Z and Z' may be identical or different and selected among a thiol group, a thiol-reactive group, an activated carboxy, —CONHNH$_2$ etc. For a definition of these groups se below under the heading Novel Reagents.

The method we have used for the conjugates employed in the experimental part comprises the steps of:

(i) reacting the antibody or the superantigen with an organic reagent containing a thiol-reactive group and an amino-reactive group to the formation of an antibody or a superantigen carrying the thiol-reactive group, and

(ii) reacting the remaining part of the superantigen and the antibody with an organic reagent containing a thiol group or a protected thiol group and an amino-reactive group to the formation of a superantigen or an antibody carrying the thiol group or the protected thiol group, whereupon (iii) the obtained products from steps (i) and (ii), respectively, are reacted with each other to the formation of a conjugate in which the superantigen is linked to the antibody via a disulfide or thioether.

The coupling conditions for each group are known per se as applied to protein chemistry. The coupling may proceed stepwise or in one step by creating intermediary functional groups that may be linked to the starting material by inert spacer arms. In general the conditions under which the synthesis and purification/recovering of the conjugate take place are always non-denaturing for the proteins involved. This normally means aqueous media and a pH-value and temperature within in the ranges pH 3–10 and 0°–50° C., respectively. The exact values depend on the groups to be reacted and the conjugate to be recovered. See more under the heading Novel reagents.

Novel reagents (developed in connection with the invention)

For the chemical synthesis of conjugates having the linkage —B—, we have developed a novel heterobifunctional reagent that complies with the general formula II:

m and n have the same meaning as above for formula (I). $Z_1$ is an HS-reactive electrophilic group, thiol (—SH) or protected thiol (e.g. AcS—), with the provision that a thiol group and a hydroxy group must not be bound to one and the same carbon atom in R. Examples of HS-reactive electrophilic groups are:

(i) halogen that is bound to a saturated carbon atom, preferably in the form of an alfa-halo-alkylcarbonyl (e.g. $Z_1CH_2CO$—);

(ii) activated thiol, preferably a so called reactive disulfide (—$SSR_1$) that is bound to a saturated carbon atom;

(iii) 3,5-dioxo-1-aza-cyclopent-3-en-1-yl.

For a definition of reactive disulfide see e.g. EP-A-128, 885 which is incorporated by reference.

$Z_1'$ is an activated carboxy, i.e. an electrophilic group. Examples are carboxylic acid halides (—COCl, —COBr, and —COI), mixed carboxylic acid anhydrides (—COOOCR$_1$), reactive esters, such as N-succinimidyloxycarbonyl, —C(=NH)—OR$_2$, 4-nitrophenylcarboxylate (—CO—OC$_6$H$_4$NO$_2$) etc. R$_1$ and R$_2$ may be lower alkyl ($C_1$–$C_6$) and R$_2$ also benzyl.

One of the advantages of our novel reagents are that they result in uniform conjugate substances with regard to the integer n in the structure $(OCH_2CH_2)n$, i.e. n is the same for each individual molecule of a given conjugate substance.

Functional groups reacting with $Z_1'$ and $Z_1$ may be present on native antibody active molecules or native superantigens or can be introduced on them. The $Z_1'$ and $Z_1$ terminals can then be reacted selectively with the appropriate antibody or superantigen in a manner known per se for these types of groups.

Known techniques encompass chain elongation either starting from our novel reagent or from the compounds to be conjugated.

Chain elongation utilizing our novel reagent may e.g. result in conjugates in which —B— is:

CO binds to NH,

N= is usually bound to a sp$^2$-hybridized carbon derived from an oxidized carbohydrate structure in an antibody or a superantigen (when being a glycoprotein),

CO— is bound NH,

N= is bound as above in (2),

R, R' and R" are alkylene selected in the same way as R in formula (I). r has the same meaning as above.

The reagent (Formula II) can be prepared starting from compounds complying with formula III:

m equals an integer 1 or 2. n equals an integer 1–20, such as 2–20 or 3–9.

The synthesis of certain compounds complying with formula III with m=1 and 2, and n=1–10 have been described before (Jullien et al, Tetrahedron Letters 29(1988) 3803–06; Houghton and Southby, Synth.Commun. 19(18) (1989)3199–3209; and EP-A-410,280 (publ. 20.1.91) and Slama and Rando, Carbohydrate Research 88(1981) 213–221 and Biochemistry 19(1980)4595–4600).

Novel reagents complying with formula II can be synthesized by reacting a compound of formula III with a bifunctional reagent of formula Z—B'—Z' known per se, where Z=$Z_1$, B'=R" that is as previously defined for R and R', and Z'=activated carboxy as defined above. After the reaction the —COOH function is transformed to an activated carboxy group, e.g. $Z_1'$=activated ester, such as N-succinimidyloxycarbonyl, 4-nitrophenyloxycarbonyl, 2,4-dinitrophenyloxykarbonyl etc.

The novel compounds of formula (III) and their novel derivatives comply with polyethers having the general formula:

$$XCH_2CH_2(OCH_2CH_2—)_nOCH_2Y \qquad (IV)$$

n is an integer 2–20, preferably 3–20 or 3–9. X is $H_2N$- including the protonated form thereof ($^+H_3N$—) or substituted $H_2N$— that is transformable to $H_2N$—, preferably by hydrolysis or reduction. Examples are unsubstituted amino ($H_2N$—); nitro; amido (carbamido), such as lower acylamido (formylamido, acetylamido . . . hexanoylamido) including acylamido groups that have electron-withdrawing substituents on the alpha carbon atom of the acyl moiety and then particularly $CF_3CONH$—, $CH_3COCH_2CONH$— etc; phtalimidoyl which possibly is ring substituted; carbamato (particularly $R_1'OCONH$— and $(R_1'OCO)(R_2'OCO)N$—, such as N—(tbutyloxycarbonyl)amino (Boc), N—(benzyloxycarbonyl)amino and di(N—(benzyloxycarbonyl))amino (Z and diZ, respectively) which possibly are ring substituted; alkyl amino in which the carbon atom binding to the nitrogen atom is alpha to an aromatic system, such as N-monobenzylamino and dibenzylamino, N-tritylamino (triphenylmethylamino) etc including analogous groups where the methyl carbon atom (including benzylic carbon atom) atom is replaced with a silicon atom (Si), such as N,N-di(tert-butylsilyl)amino; and 4-oxo-1,3,5-triazin-1-yl including such ones that are substituted with lower alkyl in their 3- and/or 5-positions.

Above and henceforth $R_1'$ and $R_2'$ stand for lower alkyl, particularly secondary and tertiary alkyl groups, and a methyl group that is substituted with 1–3 phenyl groups that possibly are ring substituted. Lower alkyl and lower acyl groups have 1–6 carbon atoms.

Y is carboxy (—COOH including —COO$^-$) or a group that is transformable to carboxy, preferably by hydrolysis or oxidation. The most important groups are the ester groups in which the carbonyl carbon atom or the corresponding atom in ortho esters binds to the methylene group in the right terminal of formula (I). Examples are alkyl ester groups (—COOR$_1'$); ortho ester groups (—C(OR$_3'$)$_3$) and reactive ester groups as defined above. R$_3'$ has the same meaning as previously defined for R$_1$, Other groups Y are —CHO, —CN, —CONH$_2$, —CONR$_1'$R$_2'$ where R$_1'$ and R$_2'$ have the same meaning as previously.

The compound of formula IV may be synthesized from known starting materials by combining methods that are known per se. Appropriate synthetic routes are:

A. Formation of the chain.
B. Transformation of terminal functional groups.
C. Transformation of a symmetric polyether to an unsymmetric ether.
D. Splitting of a bisymmetric chain into two identical fragments.

Convenient starting materials that have the repeating unit —OCH$_2$CH$_2$— are commercially available. Examples are oligoethylene glycols having 2 to 6 repeating units. Other suitable compounds with identical terminal groups are corresponding dicarboxylic acids and diamines.

Convenient starting materials that have different terminal groups are omega-hydroxy monocarboxylic acids in which the terminal groups are spaced apart by a pure polyethyleneoxide bridge. Such compounds having up to 5 repeating units have been described in the prior art (Nakatsuji, Kawamura and Okahara, Synthesis (1981) p.42).

Pharmaceutical compositions and their manufacture

The pharmaceutical composition of the invention comprises formulations that as such are known within the field but now containing our novel conjugate. Thus the compositions may be in the form of a lyophilized particulate material, a sterile or aseptically produced solution, a tablet, an ampoule etc. Vehicles, such as water (preferably buffered to a physiologically pH-value such as PBS) or other inert solid or liquid material may be present. In general terms the compositions are prepared by the conjugate being mixed with, dissolved in bound to or otherwise combined with one or more water-insoluble or water-soluble aqueous or non-aqueous vehicles, if necessary together with suitable additives and adjuvants. It is imperative that the vehicles and conditions shall not adversely affect the activity of the conjugate. Water as such is comprised within the expression vehicles.

Administration and methods of use.

Normally the conjugates will be sold and administered in predispensed dosages, each one containing an effective amount of the conjugate that, based on the result now presented, is believed to be within the range 10 μg–50 mg. The exact dosage varies from case to case and depend on patient's weight and age, administration route, type of disease, antibody, superantigen, linkage (—B—) etc.

The administration route is as commonly known within the field, i.e. a target cell lysing effective amount or a therapeutically effective amount of a conjugate according to the invention is contacted with the target cells. For the indications specified above this mostly means parenteral administration, such as injection or infusion (subcutanously, intravenously, intra-arterial, intramuscularly) to a mammal, such as a human being. The conjugate may be administered locally or systemically to the individual to be treated.

By "target cell lysing effective amount" is contemplated that the amount is effective in activating and directing CTLs to destroy the target cell.

The invention is defined in the appended claims that are part of the description. The invention will now be illustrated by a number of embodiments that in no way limit the general concept we have discovered. The experimental part presents in Part I the chemical synthesis of conjugates and in Part II effects of the conjugates prepared in example 4 on the activation of T-Cells for lysing target cells.

EXPERIMENTAL PORTION PART 1

PREPARATION OF omega-AMINO-PEG-CARBOXYLIC ACID

Isopropyl 8-hydroxy-3,6-dioxa-octanoate (1).

Sodium (23 g, 1.0 mole) in form of chips was added in portions to diethylene glycol (500 ml) under nitrogen atmosphere. When the sodium had reacted completely, the mixture was cooled to room temperature and bromoacetic acid was added (76 g, 0.5 mole) under stirring. After 18 hours at 100° C. the excess of diethylene glycol was distilled off at about 4 mm Hg. Thereafter isopropyl alcohol (400 ml) and in portions acetyl chloride (51 g, 0.65 mole) were added. After stirring for 18 hours at 65° C. the mixture was cooled to room temperature and neutralized with sodium acetate (3.5 g, 0.15 mole). The mixture was filtered and the filtrate evaporated nearly to dryness, whereupon it was dissolved in water (200 ml). The water phase was extracted with 1,1,1-trichloroethane (3×50 ml). The pooled organic phases were washed with water (20 ml). The product was extracted from the pooled water phases with dichloromethane (50 ml) that after evaporation gave an oil (55 g).

Isopropyl 11-hydroxy-3,6,9-trioxa-undecanoate (2).

Sodium (23 g, 1.0 mole) in form of chips was added in portions to triethylene glycol (700 ml) under nitrogen atmosphere. When the sodium had reacted completely, the mixture was cooled to room temperature and bromoacetic acid was added (76 g, 0.5 mole) under stirring. After 18 hours at 100° C. the excess of diethylene glycol was distilled off at about 4 mm Hg. Thereafter isopropyl alcohol (400 ml) and in portions acetyl chloride (51 g, 0.65 mole) were added. After stirring for 18 hours at 65° C. the mixture was cooled to room temperature and neutralized with sodium acetate (3.5 g, 0.15 mole). The mixture was filtered and the filtrate evaporated nearly to dryness, whereupon it was dissolved in water (200 ml). The water phase was extracted with 1,1,1-trichloroethane (3×50ml). The pooled organic phases were washed with water (20 ml). The product was extracted from the pooled water phases with dichloromethane (50 ml) that after evaporation gave an oil.

$^1$H-n.m.r.(CDCl$_3$); 1.26(d,6H);3.07(s,2H);3.6–3.8(m,12H); 4.11(s,2H);5.09(m,1 H)

8-(N-phtalimidoyl)-3,6-dioxa-octanol (3).

8-Chloro-3,6-dioxa-octanol (365 g, 2.2 mole, prepared from from triethylene glycol and SOCl$_2$) was dissolved in dimethyl formamide (400 ml) and potassium phtalimide (370 g, 2.0 mole) was added under stirring. After stirring for 18 hours at 110° C. dimethyl formamide was distilled off at reduced pressure. The residue was suspended in toluene (1.5 l) at 40°–50° C. and potassium chloride was filtrated off. The product crystallizes at cooling (–10° C.). A second fraction is available from the mother liquor by concentrating it and repeating the crystallization procedure.

$^1$H-n.m.r.(CDCl$_3$); 2.90(s,$_1$H);3.51–3.58(m,2H);3.60–3.68 (m,6H);3.73–3.78(t,2H);3.89–3.94(t,2H);7.70–7.89(m, 4H).

Isopropyl 17-(N-phtalimidoyl)-3,6,9,12,15-pentaoxa-heptadecanoate (4).

A solution of pyridine (2.8 ml, 35 mmole) in dichloromethane (30 ml) was added dropwise under stirring at about –5° C. to a solution of 8-(N-phtalimidoyl)-3,6-dioxa-octanol (3) (8.5 g, 36 mmole) and trifluoromethanesulfonic acid anhydride (10.2 g, 36 mmole) in dichloromethane. After about 30 minutes the organic phase was washed with 0.5M hydrochloric acid and water. After drying (Na$_2$SO$_4$) and filtration isopropyl 8-hydroxy-3,6-dioxa-octanoate (1) (12 g, 48 mmole) and Na$_2$PO$_4$ (6.5, 46 mmole) were added, and the mixture was vigorously stirred for 20 hours at room temperature. The reaction mixture was filtrated and the filtrate evaporated. The residue was partitioned between 1,1,1-trichloroethane and water. Evaporation of the organic phase resulted in an oil (13 g).

$^1$H-n.m.r.(CDCl$_3$);1.26(d,6H);3.58–3.76(m,18H);3.90(t, 2H); 4.11(s,2H);5.09(m,1H);7.70–7.89(m,4H).

17-(N-phtalimidoyl)-3,6,9,12,15-pentaoxa-heptadecanoic acid (5).

Isopropyl 17-(N-phtalimidoyl)-3,6,9,12,15-pentaoxa-heptadecanoate (4) (13 g) was dissolved in tetrahydrofuran (50 ml) and hydrochloric acid (conc., 50 ml)). After 16 hours at room temperature the solution was diluted with water (200 ml) and tetrahydrofuran was removed at reduced pressure. The water phase was washed with toluene (1×) and extracted with dichloromethane (2×). Drying (Na$_2$SO$_4$) and evaporation of the organic phase resulted in the product in form of an oil (8.5 g)

$^1$H-n.m.r.(CDCl$_3$): 3.57–3.76 (m,18H);3.91(t,2H);4.11(s, 2H); 4.8(br,2H);7.65–7.90(m,4H)

Isopropyl 17-amino-3,6,9,12,15-pentaoxa-heptadecanoate (6)

17-(N-phtalimidoyl)-3,6,9,12,15-pentaoxa-heptadecanoic acid (5) (8.5 g) was dissolved in 150 ml ethanol and 3 ml hydrazine hydrate. The solution was stirred at room temperature for 16 hours, whereupon HC1 (100 ml, 3M) was added and the solution was then refluxed for 3 hours. After cooling to room temperature and filtration, pH was adjusted (pH 9, NaOH) and the filtrate was evaporated almost to dryness. Water was added and re-evaporation almost to dryness was carried out, whereupon the pH of the solution was adjusted (pH 4, HC1) followed by evaporation to dryness. The product was treated with isopropanol (100 ml) and acetyl chloride (2 ml) at room temperature during the night and evaporated. The residue was collected in water and extracted into dichloromethane at an alkaline pH (7–11). Evaporation resulted in the product (3.3 g).

$^1$H-n.m.r.(CH$_3$OD): 1.26(d,6H);3.17(t,2H);3.65–3.80(m, 18H); 4.16(s,2H);5.07(m,1H)

FORMULAE OF SYNTHESIZED AMINO-PEG-CARBOXYLIC ACIDS

Compound 1:n=1

Compound 2:n=1

Compound 3, PhtN—=N-phtalimidoyl

Compound 4, PhtN—=N-phtalimidoyl

Compound 5

Compound 6

PREPARATION OF BIFUNCTIONAL REAGENTS AND COUPLING PRODUCTS

Structural formulae are set forth on a separate page.

Example 1

Preparation of N-hydroxysuccinimide ester of 17-iodoacetylamino-3,6,9,12,15 pentaoxaheptadecanoic acid A. Preparation of 17-iodoacetylamino -3,6,9,12,15-pentaoxaheptadecanoic acid (A)

Isopropyl 17-amino-3,6,9,12,15-pentaoxahepta-decanoate (see part I of the experimental part) (1.1 g, 3.2 mmole) was dissolved in 3 ml of 1M sodium hydroxide solution and left at room temperature for 30 min. 1.5 ml of 6M hydrochloric acid was added and the mixture was evaporated to dryness. The residue was taken up in dichloromethane and filtered to give 545 mg of 17-amino-3,6,9, 12,15-pentaoxa-heptadecanoic acid after evaporation of the solvent. 460 mg (1,39 mmoles) of this compound were dissolved in 10 ml of borate buffer pH 8.4. The solution was deaerated with nitrogen gas. A solution of 432 mg (1.52 mmoles) of N-succinimidyl 2-iodoacetate in 5 ml of dioxane was added dropwise during 1 min pH was kept at 8.4 by addition of 5M NaOH. The reaction solution was stirred for 15 min during inlet of nitrogen gas. According to thin layer chromatography (eluent: $CH_2Cl_2$—MeOH 60:35) the reaction was completed in some few minutes. After 15 min the pH of the reaction solution was adjusted to 3 and the solution was frozen and lyophilized. The reaction mixture was fractionated on a reversed phase column PEP—RPC HR 30/26 (Pharmacia Biosystems AB) using a gradient of 0–13% acetonitrile with 0.1% tri-fluoroacetic acid followed by isocratic separation at 13% acetonitrile, 0.1% TFA. Fractions from the desired peak were pooled and lyophilized giving 351 mg of 17-iodoacetylamino-3,6,9,12,15-pentaoxa-heptadecanoic acid (A). Yield: 76%.

The structure of the product was established by the aid of its NMR spectrum. $^1H$ NMR spectrum ($D_2O$) expressed as δ-values:

$$IC\underline{H}_2C\underset{\|}{\overset{\|}{O}}\ 4.23\ s,\quad OC\underline{H}_2C\underset{\|}{\overset{\|}{O}}H\ 3.76\ s\quad -OC\underline{H}_2C\underline{H}_2O-\ 3.71-3.76,$$

$$-NHCH_2C\underline{H}_2O-\ 3.65\ t,\quad -NHC\underline{H}_2CH_2O-\ 3.41$$

B. Preparation of N-hydroxysuccinimide ester of 17-iodoacetylamino-3,6,9,12,15-pentaoxaheptadecanoic acid (B)

Hydroxysuccinimide (4.5 mg, 39 μmole) was weighed in the reaction vial. 17-Iodoacetylamino-3,6,9,12,15-pentaoxaheptadecanoic acid (A) (18.3 mg, 39 μmole) was dissolved in 0.55 ml dried dioxane and added to the reaction vial. The vial was deareated with nitrogen gas and then a solution of 8.0 mg (39 μmole) dicyclohexylcarbodiimide in 0.15 ml of dried dioxane was added dropwise to the reaction vial. The vial was filled with nitrogen gas, closed and placed in the dark. The reaction solution was stirred for 3.5 h. The precipitate formed was removed by filtration. The percentage formed product B in the filtrate was determined by NMR-analysis to be 89%.

Example 2
Preparation of (17-iodoacetylamino-3,6,9,12,15-pentaoxaheptadecanoylamino)-immunoglobulin (C)

A. Monoclonal antibody Mab C215

A monoclonal antibody of immunoglobulin class IgG2a (Mab C215) (34 mg, 0.218 μmole) dissolved in 17.7 ml of 0.1M borate buffer pH 8.1 containing 0.9% sodium chloride was added to a reaction vial. 146 μl of a dioxane solution containing 3.6 mg (6.4 μmole) of N-hydroxysuccinimide ester of 17-iodoacetylamino-3,6,9,12,15-pentaoxaheptadecanoic acid (B) was injected into the buffer solution and the reaction was completed during stirring for 25 min. at room temperture. The reaction vial was covered with foil to exclude light. Excess of reagent B was removed by fractionation on a Sephadex G 25 K 26/40 column using 0.1M phosphate buffer pH 7.5 containing 0.9% sodium chloride as eluent. Fractions containing the desired product C were pooled. The solution (22 ml) was concentrated in an Amicon cell through a YM 30 filter to 8 ml. The concentration and degree of substitution were determined with amino acid analysis to be 4.7 mg/ml and 18 spacer per Mab C215 respectively.

B. Monoclonal antibody Mab C242

A monoclonal antibody (Mab C242) of the immunoglobulin class IgG 1 was reacted with 15, 20 and 22 times molar excess of N-hydroxysuccinimide ester of 17-iodoacetyl-amino-3,6,9,12,15-pentaoxaheptadecanoic acid (B) respectively according to the procedure described in example 2.A giving nona, dodeca and tetradeca(17-iodoacetylamino)-3, 6,9,12,15-pentaoxaheptadecanoylamino)-Mab C242. (C)

C. Monoclonal antibody Mab C

A monoclonal antibody (Mab C) of the immunoglobulin class IgG 2a was reacted with 14 and 18 times molar excess of N-hydroxysuccinimide ester of 17-iodoacetylamino-3,6, 9,12,15-pentaoxaheptadecanoic acid (B) respectively according to the procedure described in example 2A giving tetra and hepta(17-iodoacetylamino-3,6,9,12,15-pentaoxa-heptadecanoylamino)-Mab C. (C)

Example 3
Preparation of 2-mercaptopropionylamino-$Eu^{3+}$-labelled-staphylococcal enterotoxin A (SEA)

A. Preparation of $Eu^{3+}$ labelled SEA (D)

SEA (freezed dried product from Toxin Technology Inc.) (2 mg, 72 nmole) was dissolved in 722 μl milli-Q water and added to a 15 ml polypropylene tube. 100 μl of 0.1M borate buffer pH 8.6 was added and then 2160 nmoles of $Eu^{3+}$-chelate reagents (Pharmacia Wallac Oy) in 178 μl of milli-Q. The reaction was completed at room temperature over night. Excess reagent was removed by fractionation of the reaction solution on a Sephadex G 25 PD 10 column (Pharmacia Biosystems AB) using 0.1M phosphate buffer pH 8.0 as eluent. Fractions with the desired product D were pooled. The solution (3 ml) was concentrated in an Amicon cell through an YM5 filter to a volume of 0.8 ml. The concentration was determined with amino acid analysis to be 1.7 mg/ml. The degree of substitution was determined by comparing with a $EuCl_3$ standard solution to be 0.8 $Eu^{3+}$ per SEA.

B1. Preparation of 3-(2-pyridyldithio)propionylamino $Eu^{3+}$ labelled SEA (E) and 3-mercaptopropionylamino $Eu^{3+}$ labelled SEA (F)

$Eu^{3+}$ -SEA (1.24 mg, 44.8 nmoles) in 0.75 ml of 0.1M phosphate buffer pH 8.0 was added to a 15 ml polypropylene tube. 35 μl (180 nmole) of a solution of 1.6 mg of N-succinimidyl 3-(2-pyridyldithio)-propionate in 1 ml of ethanol was added to the tube and the reaction solution was stirred for 30 min at room temperature. The obtained product E was not isolated before being reduced to product F.

To the reaction solution from above were added 20 μl of 0.2M $Eu^{3+}$-citrate solution and 50 μl of 2M acetic acid to adjust the pH to 5. Thereafter a solution of 3.1 mg of dithiotreitol (Merck) in 0.1 ml of 0.9% sodium chloride was added and the reaction solution was stirred for 20 min at room temperature. Thereafter the total volume was adjusted to 1 ml by addition of 50 μl of 0.9% sodium chloride solution. The reaction solution (1 ml) was placed on a Sephadex G25 NAP-10 column (Pharmacia Biosystems AB) and desired product F was eluted by addition of 1.5 ml of 0.1M phosphate buffer pH 7.5 containing 0.9% sodium chloride. The eluted product F was collected in a 15 ml polypropylene tube and immediately used in the synthesis of product G to avoid reoxidation to a disulfide compound.

B2. Preparation of 2-mercaptopropionylaminostaphylococcal enterotoxin A (SEA) (F2)

Native SEA (freeze dried product from Toxin Technology Inc) or recombinant prepared SEA (rSEA) was reacted with 2 times molar excess of N-succinimidyl 3-(2-pyridyldithio) -propionate according to the procedure described in example 3B1.

The degree of substitution was determined with UV-analysis according to Carlsson et al (Biochem. J. 173 (1978)723–737) to be 1.9 mercaptopropionyl group per SEA.

Example 4

Preparation of the SEA-monoclonal antibody conjugate (G1 och G2)

A. Conjugates between $Eu^{3+}$-SEA and Mab C215 (G1)

To the solution of 4-mercaptopropionylamino $Eu^{3+}$ labelled SEA (F) described in example 3B was added 1.2 ml of a solution of octadeca(17-iodoactylamino-3,6,9,12,15-pentaoxaheptadecanoylamino)Mab C215 (C) (4 mg) in 0.1M phosphate buffer pH 7.5 containing 0.9% sodium chloride. The reaction was completed by standing at room temperature over night. Unreacted iodinealkyl groups were then blocked by addition of 5 μl (1.2 μmole) of a solution of 20 μl mercaptoethanol in 1 ml of water. The reaction solution was left for 4 h at room temperature and then filtrated. The filtrate was then fractionated on a Superose 12 HR 16/50 column (Pharmacia Biosystems AB) using as eluent 0.002M phosphate buffer pH 7.5 containing 0.9% sodium chloride. Fractions with the desired product G were pooled and analysed. The protein content was 0.22 mg/ml determined by amino acid analysis. The degree of substitution was one SEA per IgG determined by $Eu^{3+}$ determination. The product was also studied for immunostimulating properties and antibody binding capacity.

By increasing the amount of compound (F) in relation to compound (C) higher degree of substitution was obtained.

B. Conjugates between rSEA and Mab C215 (G2)

Octadeca (17-iodoacetylamino-3,6,9,12,15-pentaoxaheptadecanoylamino)Mab C215 (C) was reacted with 1.8 times molar excess of 2-mercaptopropionylamino-rSEA (F2) according to the procedure described in example 4A. The composition of the conjugate was analysed by sodium dodecylsulfate polyacrylamide gel electrophoresis (SDS-PAGE) on Phast-Gel™ gradient 4–15 and the bonds were scanned with Phast IMAGE (Pharmacia Biosystems AB). The conjugate obtained was composed of 6% Mab C215 with three SEA, 15% with two SEA, 28% with one SEA and 51% unsubstituted Mab C215.

In another experiment 2.7 times molar excess of F2 was used giving a conjugate with the composition 15% Mab C215 with three SEA, 25% with two SEA, 34% with one SEA and 26% of unsubstituted Mab C215.

C. Conjugates between rSEA and Mab C242

C1. Tetradeca(17-iodoacetylamino-3,6,9,12,15-pentaoxaheptadecanoylamino)Mab C242 (C) was reacted with 3.2 times molar excess of 2-mercaptopropionylamino-rSEA (F2) according to the procedure described in example 4A. The composition of the conjugate was analysed as described in example 4 B and was found to be 4% Mab C242 with four SEA, 12% with three SEA, 28% with two SEA, 36% with one SEA and 20% of unsubstituted Mab C242.

The same reaction was run but the reaction product was treated 4 h with 0.2M hydroxylamine before column fractionation to remove unstable bonds between Mab C242 and the spacer and between SEA and the mercaptopropionyl group. The conjugate formed had the composition 1% Mab C242 with four SEA, 12% with three SEA, 27% with two SEA, 36% with one SEA and 24% of unsubstituted Mab.

C2. Dodeca(17-iodoacetylamino-3,6,9,12,15-pentaoxaheptadecanoylamino)Mab C242 (C) was reacted with 3 times molar excess of 2-mercaptopropionylamino-rSEA (F2) according to the procedure described in example 4A. The conjugate obtained had the composition 6% Mab C242 with three SEA, 26% with two SEA, 36% with one SEA and 31% unsubstituted Mab C242.

C3. Nona(17-iodoacetylamino-3,6,9,12,15-pentaoxaheptadecanoylamino)Mab C242 (C) was reacted with 3 times molar excess of 2-mercaptopropionylamino-rSEA (F2) according to the procedure described in example 4A.

The conjugate obtained had the composition 13% Mab C242 with two SEA, 39% with one SEA and 46% unsubstituted Mab C242.

D. Conjugates between rSEA and Mab C

D1. Hepta(17-iodoacetylamino-3,6,9,12,15-pentaoxaheptadecanoylamino)Mab C was reacted with 5.4 times molar excess of 2-mercaptopropionylamino-rSEA (F2) according to the procedure described in example 4A. The composition of the conjugate was analysed as described in example 4B and was found to be 15% with four SEA, 24% with three SEA, 29% with two SEA, 19% with one SEA, 3% unsubstituted Mab C and 10% in a dimeric form.

The same reaction was run with 0.2M hydroxylamine present to remove unstable bonds between Mab C and spacer and between SEA and the mercaptopropionyl group. The conjugate formed had the following composition 11% Mab C with three SEA, 24% with two SEA, 30% with one SEA, 18% of unsubstituted Mab C and 17% in a dimeric form.

D2. Tetra(17-iodoacetylamino)-3,6,9,12,15-pentaoxaheptadecanoylamino)Mab C was reacted with 5.7 times molar excess of 2-mercaptopropionylamino-rSEA (F2) according to the procedure described in example 4B. The conjugate had the following compositon 8% Mab C2 with four SEA, 18% with three SEA, 30% with two SEA, 26% with one SEA, 5% of unsubstituted Mab C and 12% in a dimeric form.

Example 5

Preparation of [17-(3-mercaptopropionylamino)-3,6,9,12,15-pentaoxaheptadecanoylamino]-rSEA (I)

A. Preparation of 17-[3-(2-pyridyldithio) propionylaminol-]3,6,9,12,15-pentaoxaheptadecanoylamino)-rSEA (H)

A solution of N-hydroxysuccinimide ester of 17-[3-(2-pyridyldithio)propionylamino]-3,6,9,12,15-pentaoxaheptadecanoic acid (K) (0.53 mg (896 nmoles) in 43 μl of dioxane) was injected into a solution of 3.67 mg (128 nmoles) of rSEA in 1 ml of 0.1M phosphate buffer pH 7.5 containing 0.9% of sodium chloride. The reaction was completed in 30 min at room temperature. 100 μl was taken for analysation of degree of substitution. The rest was stored frozen until it was reduced to product I.

The degree of substitution was determined by desalting 100 μl of the reaction solution on a Sephadex G50 NICK column (Pharmacia Biosystems AB) and analysing the eluate with UV-spectroscopy according to Carlsson et al (Biochem. J. 173(1978)723–737). 2.7 spacers were coupled to rSEA.

B. Preparation of [17-(3-mercaptopropionylamino)-3 6,9,12,15-pentaoxaheptadecanoylamino]-rSEA (I)

The pH of the reaction solution with product H (0,9 ml) was adjusted with 2 HC1 to pH 4.4 and 2.9 mg of dithiotreitol dissolved in 75 μl 0.9% sodium chloride was added. The reduction was completed in 30 min. The reaction solution was added to a Sephadex G25 NAP 10 column (Pharmacia Biosystems AB) and eluted with 1.5 ml of 0.1M phosphate buffer pH 7.5 with 0.9% NaCl and immediately used in the synthesis of product J in example 11.

Example 6
Preparation of SEA-monoclonal antibody conjugate J with double spacer Dodeca(17-iodoacetylamino-3,6,9,12,15-pentaoxaheptadecanoylamino)Mab C242 (C) (4.2 mg, 27 nmoles in 1.0 ml of 0.1M phosphate buffer pH 7.5 with 0.9% NaCl) was reacted during 43 h with [17-(3-mercaptopropionylamino)-3,6,9,12,15-pentaoxaheptadecanoylamino]-rSEA (I) (1.17 mg, 42 nmoles in 1 ml of the above buffer) in the dark in nitrogen atmosphere. Thereafter 1.14 μmole of mercaptoethanol was added. After another 1 h the reaction solution was fractionated on a Superdex 200 HR 16

-continued

EXPERIMENTAL PART II

Effects of superantigen-antibody conjugates on cells

The bacterial toxin used in the following experiments was Staphylococcus enterotoxin A (SEA) obtained from Toxin Technologies (WI; USA) or produced as a recombinant protein from E. Coli.

Figure 1A:
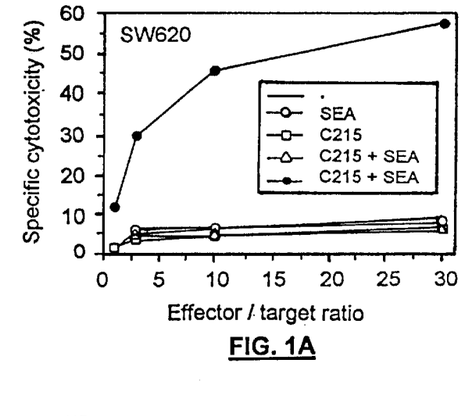
FIG. 1 shows SEA-C215 mAb conjugate directing CTLs against MHC class II colon carcinoma cells.
Figure 1B:
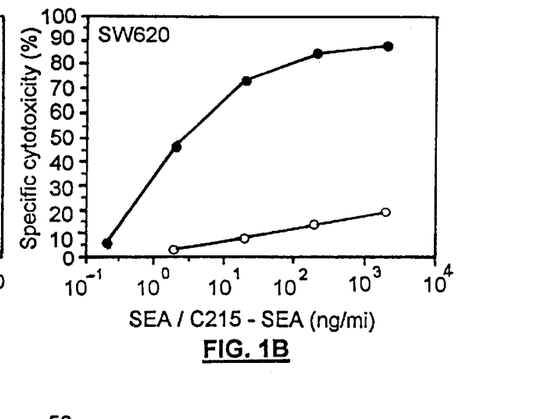
Figure 1C:
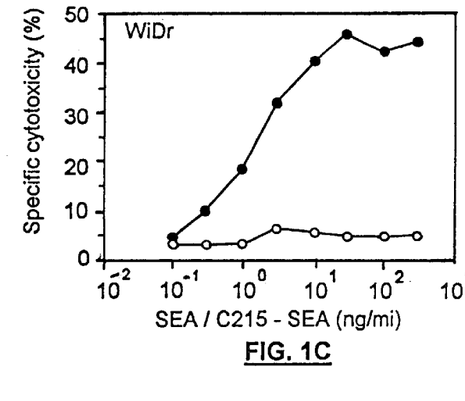
Figure 1D:
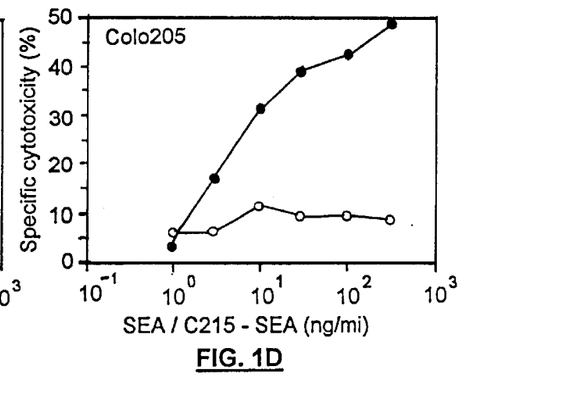
Figure 1E:
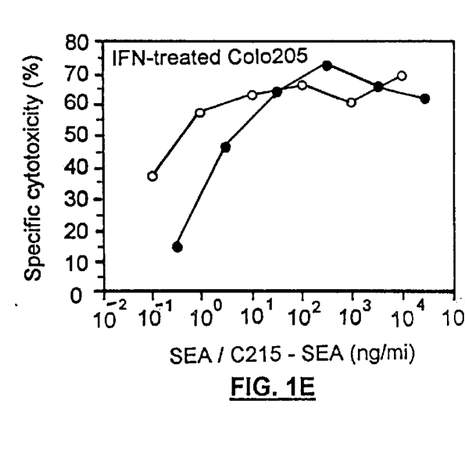
Figure 1F:
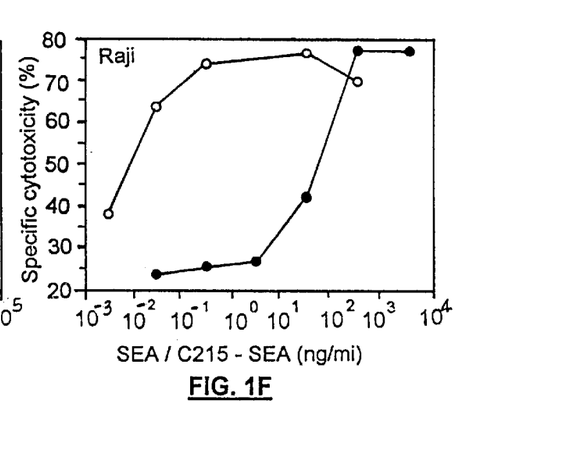
Figure 2:
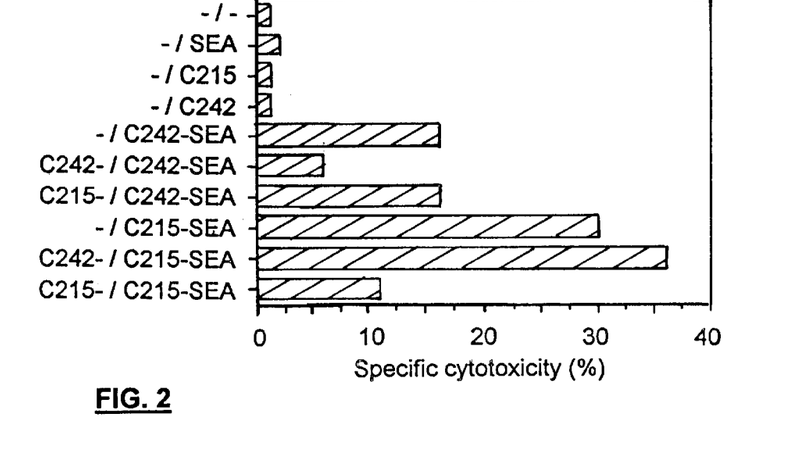
FIG. 2 shows SEA-C215 mAb conjugate and SEA-C242 mAb conjugate induced CTL targeting against colon carcinoma cells.

The antibodies were C215, C242 and Thy-1.2 mAbs. C gate to the C215 mAb molecule on the target cells, we performed blocking studies with excess of unconjugated C215 mAb and mAb C242, which bind to an irrelevant antigen on the colon carcinoma cells (in regard to C215 mAb binding). Addition of mAb C215 strongly blocked cytotoxicity, whereas the C242 mAb had no influence (FIG. 2). Similarly lysis by a SEA-C242 mAb conjugate was specifically blocked by excess of unconjugated C242 mAb but not C215 mAb.

The capacity of SEA-C215 mAb conjugate to induce T cell dependent lysis of MHC Class II SW620 colon carcinoma cells was seen in both CD4$^+$ and CD8$^+$ T cell populations (Table 2). SEA did not activate any of these T cell subsets to mediate killing of SW620 cells but induced lysis of MHC Class II$^+$ Raji cells (Table 2).

Figure 3A:
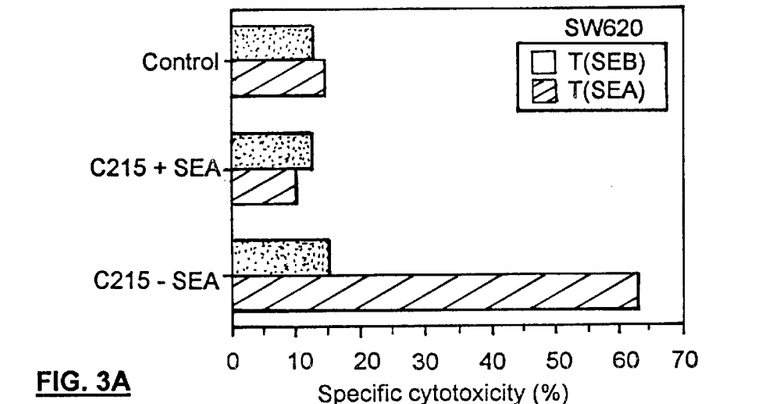
FIG. 3 shows lysis of SEA-C215 mAb conjugate coated colon carcinoma cells mediated by SEA but not by SEB responding CTLs.
Figure 3B:
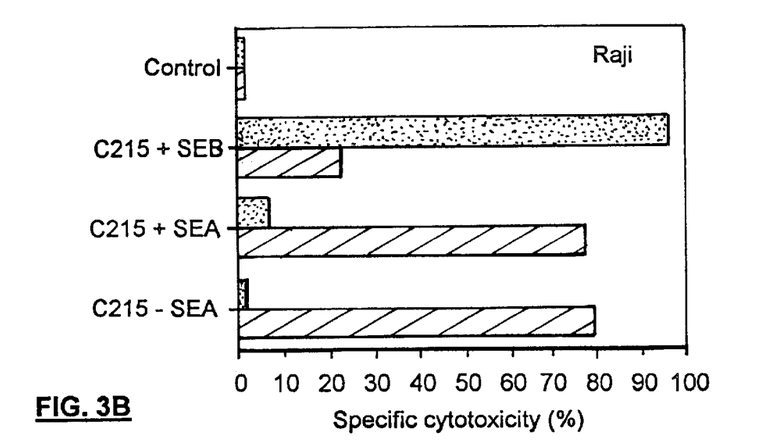
Figure 4A:
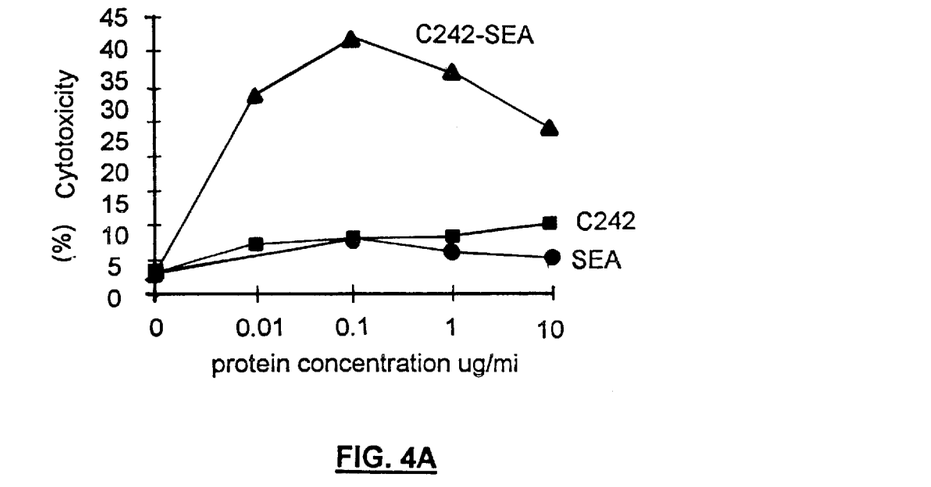
FIG. 4 shows cytotoxicity induced by SEA-C242 mAb conjugate and SEA-Anti-Thy-1.2 mAb conjugate against target cells.
Figure 4B:
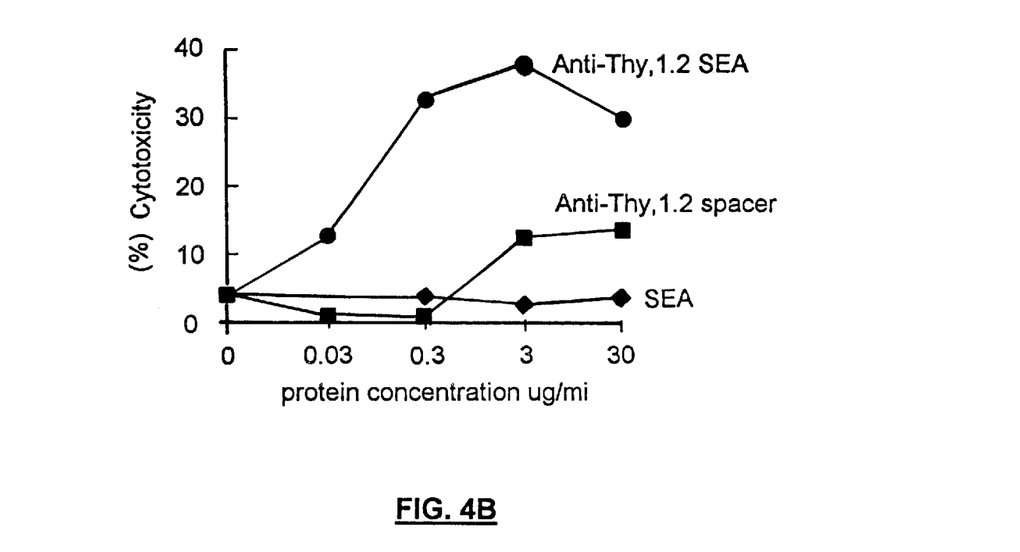

The SEA-C215 mAb conjugate induced lysis of SW620 and Raji cells by a SEA expanded T cell line, but not by a SEB expanded T cell line (FIG. 3). The specificity of the SEA and SEB lines is indicated by their selective response to SEA and SEB, respectively, when exposed to Raji cells (FIG. 4). This indicates that the SEA-C215 mAb conjugate retains similar V-beta TCR specificity as for unconjugated SEA.

Legend to figures

FIG. 1. The SEA-C215 mAb conjugate directs CTLs against MHC class II$^-$ colon carcinoma cells. Upper left panel demonstrates the effect of SEA responsive CTLs against SW620 cells at various effector to target ratios in the absence (−) or presence of SEA-C215 mAb conjugate, SEA, C215 and a mixture of C215 and SEA (C215+SEA) at a concentration of 1 µg/ml of each additive. The other panels demonstrates the capacity of SEA—C215 mAb conjugate, and SEA to target SEA responsive CTLs against the C215+ MHC class II$^-$ colon carcinoma cell lines SW620, Colo205 and WiDr, MHC class II$^+$ C215$^+$ interferon treated Colo205 cells and C215- MHC class II+Raji cells. Effector to target ratio was 30:1. Addition of unconjugated C215 mAb, at several concentrations, did not induce any CTL targeting against these cell lines. FACS analysis on SW620 cells, Colo205 and WiDr cells using mAbs against HLA—DR, —DP, —DQ failed to detect any surface MHC class II expression, whereas abundant expression of HLA—DR, —DP and —DQ was detected on Raji cells and HLA—DR and —DP on interferon treated Colo205 cells. Colo205 cells were treated with 1000 units/ml of recombinant interferon-gamma for 48 hours prior to use in the CTL assay.

FIG. 2. SEA-C215 mAb conjugate and SEA-C242 mAb conjugate induced CTL targeting against colon carcinoma cells depends on the antigen selectivity of the mAb. Lysis of Colo205 cells by a SEA responsive CTL line in the presence of SEA-C215 mAb and SEA-C242 mAb conjugate (3 µg/ml) is blocked by addition of unconjugated C215 and C242 mAbs (30 µg/ml), respectively. The unconjugated mAbs or control medium (−) were added to the target cells 10 minutes prior to the conjugates.

FIG. 3. Lysis of SEA-C215 mAb conjugate coated colon carcinoma cells is mediated by SEA but not SEB responding CTLs. Autologous SEA and SEB selective T cell lines were used at an effector to target ratio of 10:1 against SW620 and Raji target cells in the absence (control) or presence of SEA-C215 mAb conjugate, a mixture of unconjugated C215 mAb and SEA (C215+SEA) and unconjugated C215 mAb and SEB (C215+SEB) at a concentration of 1 µg/ml of each additive.

FIG. 4. Cytotoxicity induced by the SEA-C242 mAb conjugate and SEA-Anti-Thy-1.2 mAb conjugate against their target cells (Colo205 tumour cells and EL-4 tumour cells, respectively).

TABLE 1

SEA-C215 mAb conjugate bind to
C215$^+$ colon carcinoma cells and MHC Class II$^+$ Raji cells

| Reagent | Cell | Facs analysis |
| --- | --- | --- |
| SEA-C215 mAb | Colo205 | Pos |
|  | Raji | Pos |
| C215 mAb | Colo205 | Pos |
|  | Raji | Neg |
| SEA-C242 mAb | Colo205 | Pos |
|  | Raji | Pos |
| C242 mAb | Colo205 | Pos |
|  | Raji | Neg |
| SEA-anti-Thy-1.2 mAb | EL-4 | Pos |
| anti-Thy-1.2 mAb | EL-4 | Pos |
| SEA | Colo205 | Neg |
|  | Raji | Pos |
| control | Colo205 | Neg |
|  | Raji | Neg |
|  | EL-4 | Neg |

Cells were incubated with the various additives of control (PBS-BSA) for 30 minutes on ice, washed and processed as described below. The staining of C215 mAb and C242 mAb bound to Colo205 cells and anti-Thy-1.2 bound to EL-4 cells was detected using FITC labelled rabbit anti mouse 1 g. The staining of SEA to Raji cells was detected using a rabbit anti-SEA sera followed by a FITC-swine anti rabbit 1 g. The staining of SEA-C215 mAb conjugate to Colo 205 and Raji cells was detected utilizing the above described procedures for C215 mAb and SEA. FACS analysis was performed on a FACS star plus from Becton and Dickinson. Staining with second and third steps only was utilized to define the background.

TABLE 2

CD4$^+$ and CD8$^+$ CTLs lyse colon carcinoma cells presenting the C215-SEA conjugate.

| | | % cytotoxicity | | |
| --- | --- | --- | --- | --- |
| Effector$^{A)}$ | Target | control | SEA | C215-SEA |
| CD4$^+$ | SW620 | 2 | 5 | 50 |
| CD4$^+$ | Raji | 0 | 41 | 43 |
| CD8$^+$ | SW620 | 0 | 1 | 23 |
| CD8$^+$ | Raji | 2 | 72 | 68 |

$^{A)}$The CTLs (SEA-3) were used at effector to target ratios of 30:1 in the absence (control) or presence of SEA and C215-SEA at 1 µg/ml.

We claim:

1. A soluble antibody conjugate comprising a superantigen covalently linked to an antibody, wherein said antibody is specific for a cell surface structure on a cell, and said superantigen is recognized by T-Cells and capable of activating cytotoxic T-cells(CTL's).

2. A conjugate according to claim 1, wherein said antibody is monoclonal.

3. A conjugate according to claim 2, wherein said cell is associated with disease selected from the group consisting of cancer, autoimmunity, parasitic infestation, and microbial infections.

4. A conjugate according to claim 3, wherein said disease is cancer.

5. A conjugate according to claim 4, wherein said cell is a colon carcinoma.

6. A conjugate according to claim 3, wherein said surface structure is a C242 epitope.

7. A conjugate according to claim 3, wherein there are 1 to 5 superantigen moieties per antibody moieties.

8. A conjugate according to claim 3, wherein the superantigen is of bacterial origin.

9. A conjugate according to claim 3, wherein the superantigen is a staphylococcal enterotoxin.

10. A conjugate according to claim 9, wherein the superantigen is SEA.

11. A conjugate according to claim 2, wherein the surface structure is a C242 epitope and the superantigen is SEA.

12. A conjugate according to claim 2, wherein the superantigen and antibody are held together through a covalent organic linkage structure B which comprises at least one amide structure.

13. A conjugate according to claim 12, wherein the linkage B comprises the structure —$S_r$RCONHCH$_2$CH$_2$(OCH$_2$CH$_2$)$_n$O(CH$_2$)Coy—(I) wherein r is an integer 1 or 2

R is alkylene having 1–4 carbon atoms;

n is an integer from 1–20;

m is an integer 1 or 2; and

Y is —NH—, —NHNH— or —NHN=CH—.

14. A method for the lysis of a target cell, by assistance of T-cells, wherein the target cells are contacted with a target cell lysis effective amount of a soluble antibody conjugate comprising a monoclonal antibody or an antibody fragment linked to a superantigen; wherein said monoclonal antibody or antibody fragment is specific for a cell surface structure on said target cell, and said superantigen is recognized by T-cells and capable of activating cytotoxic T-cells (CTL's).

15. A method for the treatment of a mammal, including a human individual, suffering from a disease selected from the group consisting of cancer; autoimmunity; an infection caused by a virus, a bacteria or fungi; and an infestation caused by a parasite, said method comprising administering to said mammal a target cell lysis effective amount of a conjugate according to claim 1.

16. A method according to claim 14, wherein said target cell is associated with disease selected from the group consisting of cancer, autoimmunity, parasitic infestation, and microbial infections.

17. A method according to claim 16, wherein said disease is cancer.

18. A method according to claim 17, wherein said target cell is a colon carcinoma cell.

19. A method according to claim 16, wherein said surface structure is a C242 epitope.

20. A method according to claim 16, wherein there are 1 to 5 superantigen moieties per antibody moieties.

21. A method according to claim 16, wherein the superantigen is of bacterial origin.

22. A method according to claim 16, wherein the superantigen is a staphylococcal enterotoxin.

23. A method according to claim 22, wherein the superantigen is SEA.

24. A method according to claim 16, wherein the surface structure is a C242 epitope and the superantigen is SEA.

25. A method according to claim 16, wherein the superantigen and antibody are held together through a covalent organic linkage structure B which comprises at least one amide structure.

26. A method according to claim 25, wherein the linkage B comprises the structure —$S_r$RCONHCH$_2$CH$_2$(OCH$_2$CH$_2$)$_n$O (CH$_2$)$_m$COY—(I) wherein r is an integer 1 or 2

R is alkylene having 1–4 carbon atoms;

n is an integer from 1–20;

m is an integer 1 or 2; and

Y is —NH—, —NHNH— or —NHN=CH—.

27. A method according to claim 15, wherein said disease is cancer.

28. A method according to claim 15, wherein said target cell is a colon carcinoma cell.

29. A method according to claim 15, wherein said surface structure is a C242 epitope.

30. A method according to claim 15, wherein there are 1 to 5 superantigen moieties per antibody moieties.

31. A method according to claim 15, wherein the superantigen is of bacterial origin.

32. A method according to claim 15, wherein the superantigen is a staphylococcal enterotoxin.

33. A method according to claim 32, wherein the superantigen is SEA.

34. A method according to claim 15, wherein the surface structure is a C242 epitope and the superantigen is SEA.

35. A method according to claim 15, wherein the superantigen and antibody are held together through a covalent organic linkage structure B which comprises at least one amide structure.

36. A method according to claim 35, wherein the linkage B comprises the structure —$S_r$RCONHCH$_2$CH$_2$(OCH$_2$CH$_2$)$_n$O (CH$_2$)$_m$COY—(I) wherein r is an integer 1 or 2

R is alkylene having 1–4 carbon atoms;

n is an integer from 1–20;

m is an integer 1 or 2; and

Y is —NH—, —NHNH— or —NHN=CH—.

37. A conjugate according to claim 1, wherein said antibody comprises an active antibody fragment.

38. A conjugate according to claim 4, wherein said cancer is carcinoma.

39. A conjugate according to claim 12, wherein the covalent organic linkage structure B comprises a polypeptide chain.

40. A conjugate according to claim 12, wherein the covalent organic linkage structure B is longer than 3 atoms and shorter than 100 atoms.

41. A conjugate according to claim 40, wherein the covalent organic linkage structure B comprises a polypeptide chain.

42. A conjugate according to claim 41, wherein the polypeptide chain comprises naturally occurring hydrophilic alpha amino acids.

43. A conjugate according to claim 42, wherein the polypeptide chain comprises amino acids selected from the group consisting of asparagine, glutamine, lysine, arginine, glycine, threonine, serine and histidine.

44. A conjugate according to claim 39, wherein the covalent organic linkage structure B has been recombinantly produced.

45. A conjugate according to claim 40, wherein the covalent organic linkage structure B comprises a polypeptide chain comprising naturally occurring hydrophilic alpha amino acids selected from the group consisting of asparagine, glutamine, lysine, arginine, glycine, threonine, serine and histidine.

46. A conjugate according to claim 1, wherein said target cell is a human cell.

47. A conjugate according to claim 1, wherein said disease is a human disease, and said target cell is a human tumor cell.

48. A conjugate according to claim 1, wherein said target cell is capable of being induced to express MHC Class II antigens as a consequence of conjugate activation of immune cells.

49. A conjugate according to claim 1, wherein said antibody comprises an active antibody fragment.

50. A conjugate according to claim 1, wherein the superantigen and antibody are held together through a covalent organic linkage structure B which comprises at least one amide structure, and comprises a polypeptide chain comprising naturally occurring hydrophilic alpha amino acids selected from the group consisting of asparagine, glutamine, lysine, arginine, glycine, threonine, serine and histidine.

51. A method according to claim 16, wherein said antibody comprises an active antibody fragment.

52. A method according to claim 17, wherein said cancer is carcinoma.

53. A method according to claim 25, wherein the covalent organic linkage structure B comprises a polypeptide chain.

54. A method according to claim 25, wherein the covalent organic linkage structure B is longer than 3 atoms and shorter than 100 atoms.

55. A method according to claim 54, wherein the covalent organic linkage structure B comprises a polypeptide chain.

56. A method according to claim 55, wherein the polypeptide chain comprises naturally occurring hydrophilic alpha amino acids.

57. A method according to claim 56, wherein the polypeptide chain comprises amino acids selected from the group consisting of asparagine, glutamine, lysine, arginine, glycine, threonine, serine and histidine.

58. A method according to claim 53, wherein the covalent organic linkage structure B has been recombinantly produced.

59. A method according to claim 54, wherein the covalent organic linkage structure B comprises a polypeptide chain comprising naturally occurring hydrophilic alpha amino acids selected from the group consisting of asparagine, glutamine, lysine, arginine, glycine, threonine, serine and histidine.

60. A method according to claim 16, wherein said target cell is a human cell.

61. A method according to claim 16, wherein said disease is a human disease and said target cell is a human tumor cell.

62. A method according to claim 16, wherein said target cell is capable of being induced to express MHC Class II antigens as a consequence of conjugate activation of immune cells.

63. A method according to claim 14, wherein, the superantigen and antibody are held together through a covalent organic linkage structure B which comprises at least one amide structure, and comprises a polypeptide chain comprising naturally occurring hydrophilic alpha amino acids selected from the group consisting of asparagine, glutamine, lysine, arginine, glycine, threonine, serine and histidine.

64. A method according to claim 15, wherein said antibody comprises an active antibody fragment.

65. A method according to claim 27, wherein said cancer is carcinoma.

66. A method according to claim 35, wherein the covalent organic linkage structure B comprises a polypeptide chain.

67. A method according to claim 35, wherein the covalent organic linkage structure B is longer than 3 atoms and shorter than 100 atoms.

68. A method according to claim 67, wherein the covalent organic linkage structure B comprises a polypeptide chain.

69. A method according to claim 68, wherein the polypeptide chain comprises naturally occurring hydrophilic alpha amino acids.

70. A method according to claim 69, wherein the polypeptide chain comprises amino acids selected from the group consisting of asparagine, glutamine, lysine, arginine, glycine, threonine, serine and histidine.

71. A method according to claim 66, wherein the covalent organic linkage structure B has been recombinantly produced.

72. A method according to claim 67, wherein the covalent organic linkage structure B comprises a polypeptide chain comprising naturally occurring hydrophilic alpha amino acids selected from the group consisting of asparagine, glutamine, lysine, arginine, glycine, threonine, serine and histidine.

73. A method according to claim 15, wherein said target cell is capable of being induced to express MHC Class II antigens as a consequence of conjugate activation of immune cells.

* * * * *

UNITED STATES PATENT AND TRADEMARK OFFICE
CERTIFICATE OF CORRECTION

PATENT NO. : 5,858,363
DATED : January 12, 1999
INVENTOR(S) : Mikael Dohlsen et al.

It is certified that error appears in the above-identified patent and that said Letters Patent is hereby corrected as shown below:

<u>Title Page,</u>
Section '[73] Assignee.", delete "Pharmacia & Upjohn AB, Italy" and
Insert therefor -- Pharmacia & Upjohn Aktiebolag (AB) --

Signed and Sealed this

Twenty-eighth Day of August, 2001

*Attest:*

*Attesting Officer*

NICHOLAS P. GODICI
*Acting Director of the United States Patent and Trademark Office*